(12) United States Patent
Berggren et al.

(10) Patent No.: US 10,449,020 B2
(45) Date of Patent: *Oct. 22, 2019

(54) METHOD AND ARRANGEMENT FOR FORMING A DENTAL BRIDGE

(75) Inventors: Carina Berggren, Torslanda (SE); Lars Jörneus, Frillesås (SE); Ulf Johansson, Onsala (SE); Petrus Brännvall, Göteborg (SE); Olof Vogel, Göteborg (SE)

(73) Assignee: NOBEL BIOCARE SERVICES AG, Kloten (CH)

( * ) Notice: Subject to any disclaimer, the term of this patent is extended or adjusted under 35 U.S.C. 154(b) by 1700 days.

This patent is subject to a terminal disclaimer.

(21) Appl. No.: 12/663,516

(22) PCT Filed: May 29, 2008

(86) PCT No.: PCT/EP2008/004245
§ 371 (c)(1),
(2), (4) Date: Aug. 9, 2010

(87) PCT Pub. No.: WO2008/148495
PCT Pub. Date: Dec. 11, 2008

(65) Prior Publication Data
US 2010/0291509 A1    Nov. 18, 2010

(30) Foreign Application Priority Data
Jun. 7, 2007 (EP) .................................. 07011196

(51) Int. Cl.
  *C04B 35/64* (2006.01)
  *A61C 13/00* (2006.01)
(52) U.S. Cl.
  CPC ..... *A61C 13/0022* (2013.01); *Y10T 29/49567* (2015.01)

(58) Field of Classification Search
CPC . A61C 13/0003; A61C 13/0022; C04B 35/10; C04B 35/48
(Continued)

(56) References Cited

U.S. PATENT DOCUMENTS 3,091,014 A    5/1963 Smoot et al.
3,179,724 A *  4/1965 Jones ............................. 264/607
(Continued)

FOREIGN PATENT DOCUMENTS

DE    91 13 284 U1    2/1993
DE    199 04 523 A1   8/2000
(Continued)

OTHER PUBLICATIONS

Y. Probst et al. "Le fraisage manuel de la zircone"/"The manual milling of zircon". Strategie prothetique, Sep. 2006, vol. 6, No. 4, pp. 263-271. (English language machine translation of document on IDS dated Dec. 10, 2013). [online] [retrieved on Sep. 3, 2014]. Retrieved from: Google Translate.*
(Continued)

*Primary Examiner* — Erin Snelting
(74) *Attorney, Agent, or Firm* — Knobbe, Martens, Olson & Bear, LLP

(57) ABSTRACT

Certain embodiments of the invention relate to a method of manufacturing a dental bridge. In certain embodiments of the method, a pre-sintered blank made from a green body of ceramic material is subjected to a machining operation that transforms the blank into an intermediate product with a bridge structure and a support body linked to the bridge structure by one or several retaining sections that extend from the support body to the bridge structure. In certain embodiments, a sintering operation is then performed on the intermediate product while the retaining section(s) still link(s) the support body to the bridge structure.

15 Claims, 8 Drawing Sheets

(58) Field of Classification Search
USPC .............................. 264/672, 607, 608, 673
See application file for complete search history.

(56) References Cited

U.S. PATENT DOCUMENTS

| | | | |
|---|---|---|---|
| 4,362,507 A | 12/1982 | Antonucci | |
| 4,766,704 A | 8/1988 | Brandestini et al. | |
| 5,080,589 A | 1/1992 | Oden et al. | |
| 5,106,303 A | 4/1992 | Oden et al. | |
| 5,184,306 A | 2/1993 | Erdman et al. | |
| 5,217,375 A | 6/1993 | Oden et al. | |
| 5,283,019 A | 2/1994 | Atwell et al. | |
| 5,342,201 A | 8/1994 | Oden | |
| 5,350,551 A | 9/1994 | Shino | |
| 5,565,152 A | 10/1996 | Oden et al. | |
| 5,775,912 A | 7/1998 | Panzera et al. | |
| 5,788,498 A | 8/1998 | Wohlwend | |
| 6,106,747 A | 8/2000 | Wohlwend | |
| 6,133,174 A | 10/2000 | Brodkin et al. | |
| 6,322,728 B1 | 11/2001 | Brodkin et al. | |
| 6,352,669 B1 * | 3/2002 | Cooper et al. ................ | 264/608 |
| 6,354,836 B1 | 3/2002 | Panzera et al. | |
| 6,454,629 B1 | 9/2002 | Basler et al. | |
| 6,488,503 B1 | 12/2002 | Lichkus et al. | |
| 6,508,150 B1 | 1/2003 | Bertschinger | |
| 6,808,659 B2 | 10/2004 | Schulman et al. | |
| 6,821,462 B2 | 11/2004 | Schulman et al. | |
| 6,884,969 B1 | 4/2005 | Brach et al. | |
| 6,905,293 B1 | 6/2005 | Filser et al. | |
| 7,011,522 B2 | 3/2006 | Panzera et al. | |
| 7,077,391 B2 | 7/2006 | Filser et al. | |
| 7,234,938 B2 | 6/2007 | Bodenmiller | |
| 7,556,460 B2 | 7/2009 | Steger | |
| 7,604,759 B2 | 10/2009 | Gubler et al. | |
| 7,955,159 B2 | 6/2011 | Heinz et al. | |
| 8,197,299 B2 | 6/2012 | Heinz et al. | |
| 8,231,825 B2 * | 7/2012 | Eriksson et al. ............. | 264/678 |
| 2002/0125619 A1 | 9/2002 | Bodenmiller et al. | |
| 2004/0104495 A1 | 6/2004 | Laubersheimer | |
| 2004/0119180 A1 | 6/2004 | Frank et al. | |
| 2004/0137399 A1 | 7/2004 | Fleischfresser | |
| 2005/0019121 A1 | 1/2005 | Suttor et al. | |
| 2005/0023710 A1 | 2/2005 | Brodkin et al. | |
| 2005/0037312 A1 | 2/2005 | Uchida | |
| 2006/0082033 A1 * | 4/2006 | Hauptmann et al. ......... | 264/605 |
| 2006/0168815 A1 | 8/2006 | Saliger et al. | |
| 2007/0056467 A1 | 3/2007 | Panzera | |
| 2007/0108645 A1 | 5/2007 | Von Schroeter et al. | |
| 2007/0275352 A1 * | 11/2007 | Gubler et al. ............ | 433/201.1 |
| 2008/0318189 A1 | 12/2008 | Brodkin et al. | |
| 2009/0321971 A1 * | 12/2009 | Brodkin et al. ................ | 264/17 |
| 2012/0326343 A1 | 12/2012 | Eriksson et al. | |

FOREIGN PATENT DOCUMENTS

| | | |
|---|---|---|
| DE | 103 25 524 A1 | 4/2004 |
| EP | 0 774 933 B1 | 5/1997 |
| EP | 0 943 295 A | 9/1999 |
| EP | 1 396 237 A | 3/2004 |
| EP | 1 535 587 A1 | 6/2005 |
| GB | 1 440 331 | 6/1976 |
| GB | 2 064 737 A | 6/1981 |
| JP | 2004-527280 | 9/2004 |
| JP | 2006-271435 | 10/2006 |
| WO | WO 01/12097 | 2/2001 |
| WO | WO 2004/086999 A1 | 10/2004 |
| WO | WO 2006/025778 A1 | 3/2006 |
| WO | WO 2006/031096 A1 | 3/2006 |
| WO | WO 2006/079459 A | 8/2006 |
| WO | WO 2007/147549 A | 12/2007 |

OTHER PUBLICATIONS

Filser et al. "All-Ceramic Dental Bridges by Direct Ceramic Machining (DCM)." in: Materials in Medicine, Materials Day, Department of Materials (May 1998), pp. 165-189.*
PCT/EP2008/004245 International Search Report dated Aug. 7, 2008 issued in the name of Nobel Biocare Services AG.
Extended European Search Report in European Application No. 07011197.6 dated Oct. 24, 2007.
X. Balmes, "From dream to reality," in Spectrum Dialogue, vol. 6, No. 1, Seiten 52-66, Jan. 1997.
Kennard, F., "Cold Isostatic Pressing," in *Engineered Materials Handbook*, vol. 4: Ceramics and Glasses (ASM International, 1991) pp. 147-151.
PCT/EP2008/004241 International Search Report dated Sep. 16, 2008 issued in the name of Nobel Biocare Services AG.
PCT/EP2008/010645 International Search Report dated Mar. 19, 2009 issued in the name of Nobel Biocare Services AG.
Communication of a Notice of Opposition for EP Application No. 07011197 (EP Patent No. 2000109) dated Feb. 14, 2012 (received Feb. 17, 2012).
Erklä rung Wilfried Tratter vom 2. Feb. 2012.
S. Opferkuch in dental-labor, LIII, Heft Dec. 2005, Seiten 1825-1836.
Response to Communication of a Notice of Opposition for EP Application No. 07011197 (EP Patent No. 2000109) dated Jul. 17, 2012.
Y. Mahiat, La zircone: cette méconnue, Stratégie prothétique, Feb. 2006, vol. 6, No. 1, pp. 55-65.
Y. Probst et al.: Le fraisage manuel de la zircone, Stratégie prothétique, Sep. 2006, vol. 6, No. 4, pp. 263-271.
James, P.J., "Principles of Isostatic Pressing" in *Isostatic Pressing Technology*, ed. By P.J. James (1983), Chapter 1, pp. 1-27.
Richerson, D., "Shape-Forming Processes" in *Modern Ceramic Engineering*, 2d ed. (1992), Chapter 10, pp. 418-443.
Richerson, D., "Densification" in *Modern Ceramic Engineering*, 2d ed. (1992), Chapter 11, pp. 519-529.
Feb. 19, 2015 Reply to Grounds of Appeal in EP Patent 2000109 in 102 pages.
Hannink et al., "Progress in transformation toughening of ceramics," Annual Review of Materials Science 24, 1994, 359-408.
BruxZir™ Milling Blanks—Instructions for Use in 2 pages.
Sep. 4, 2014 Grounds of Appeal in EP Patent 2000109 in 51 pages.
Erklärung von Hrn. Alexander Kirchler dated Aug. 13, 2014 in 1 page.
Versuchsbericht "Bestimmung der biaxialen Biegefestigkeit" dated Aug. 13, 2014 in 3 pages.
Erklärung von Dr. Jörg Reinshagen dated Aug. 29, 2014 in 1 page.
Messprotokol zu Ofen 10 vom Jan. 16, 2007 in 1 page.
Prüfbericht "Biaxial-Prüfung" dated Aug. 28, 2014 in 1 page.
Wieland Invoices from Sep. 5, 2007 and Oct. 5, 2007 in 6 pages.
C. Gruber, "Emotionen in Zirkondioxid," Dental Dialogue, 2006, Jg. 7, pp. 2-14.
Filser, F. et al. "All-Ceramic Dental Bridges by the Direct Ceramic Machining Process (DCM)," *Bioceramics*, vol. 10, Ed. By L. Sedel and C. Rey, *Proceedings of the 10th International Symposium on Ceramics in Medicine*, Paris, France, Oct. 1997, pp. 433-436.
Consolidated List of Cited Documents from an Opposition against EP Patent No. 2014254, dated Aug. 5, 2019, 1 page.
D1A—Ausdruck von Internetseite, www.spectrumdialogue.com, zu Artikel D1, 1 page.
D2—Tosoh Zirconia Powders, Marz 2003, 2 pages.
Opposition filed by Ivoclar Vivadent AG against EP Patent No. 2014254, dated Jul. 31, 2019, 15 pages.

* cited by examiner

Fig. 1
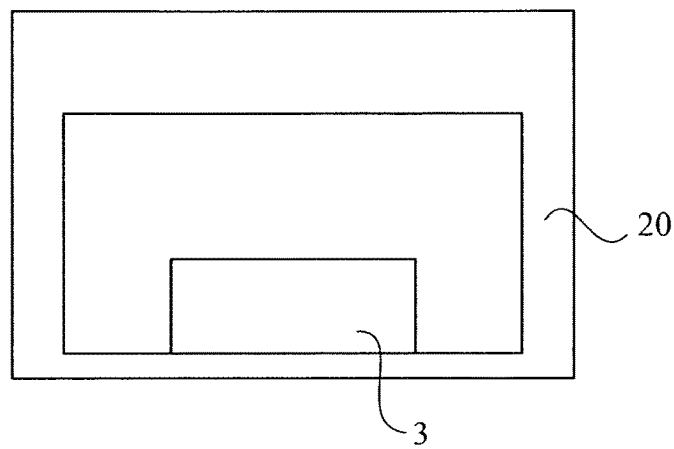
Fig. 2
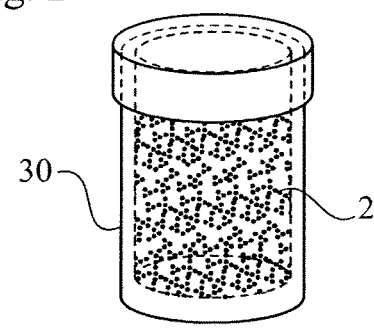
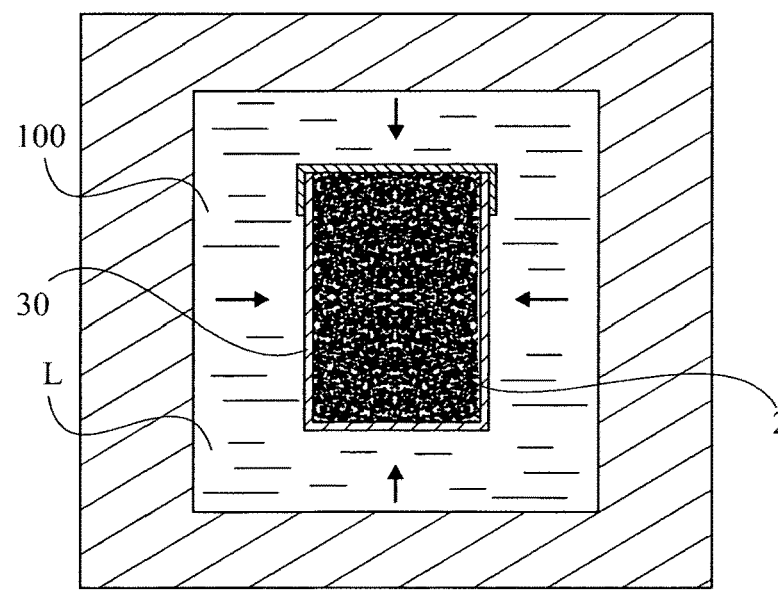
Fig. 3

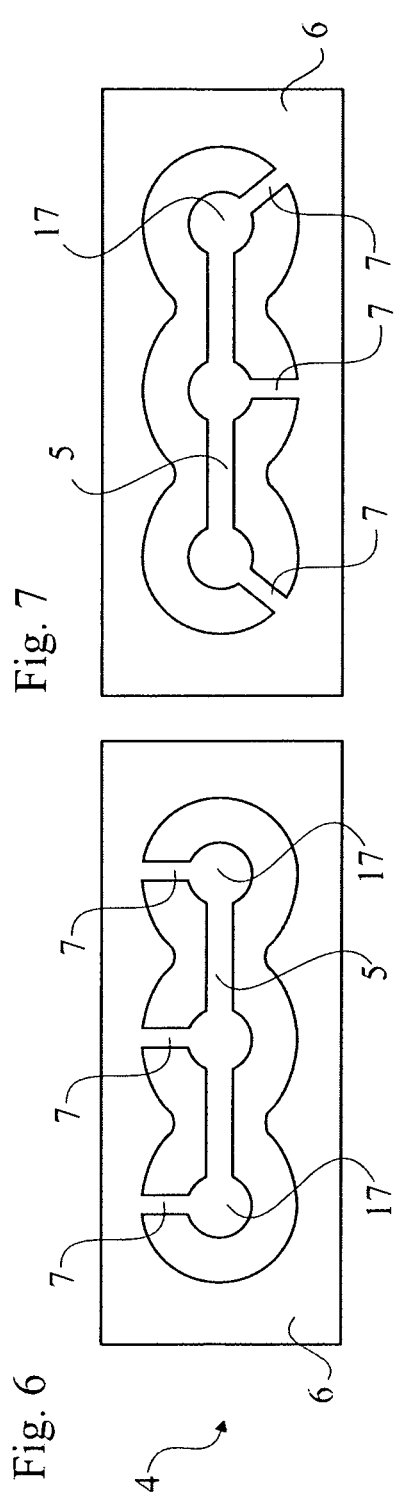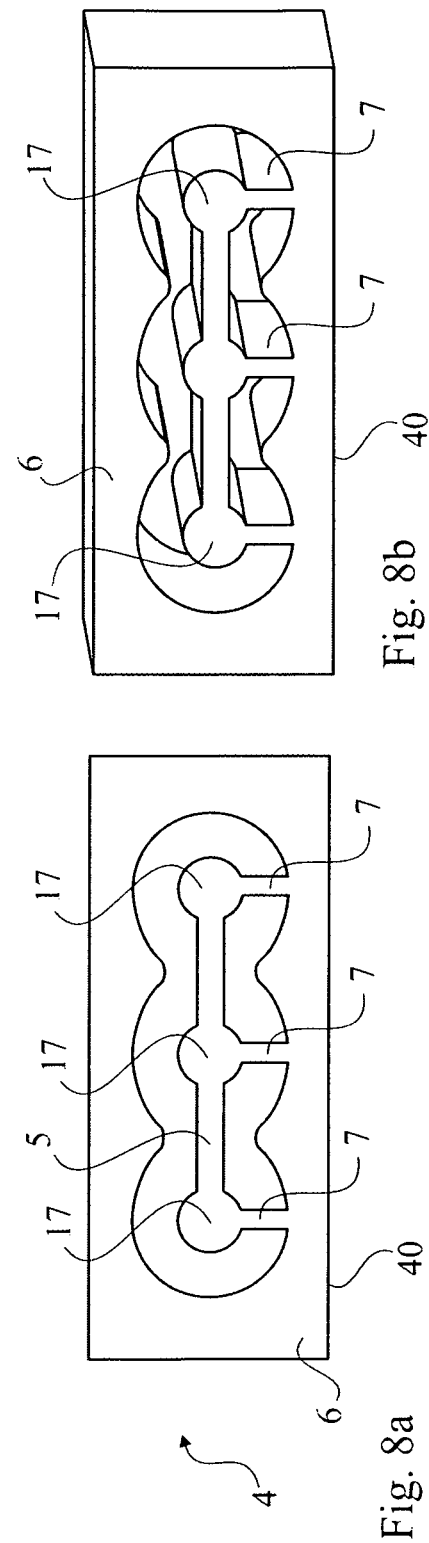

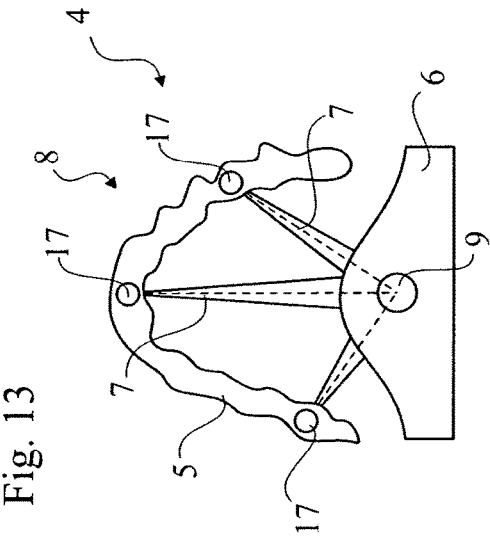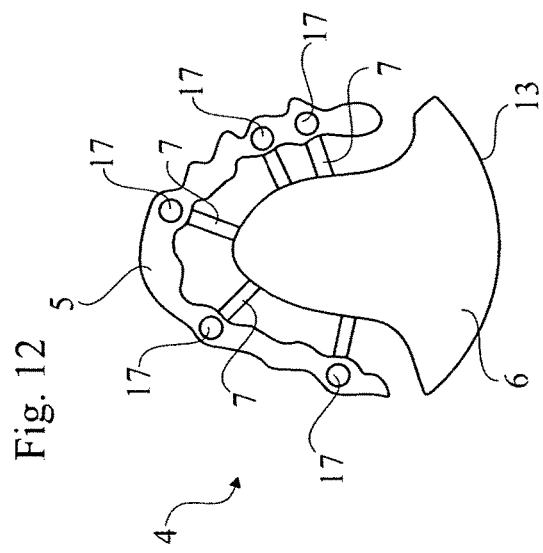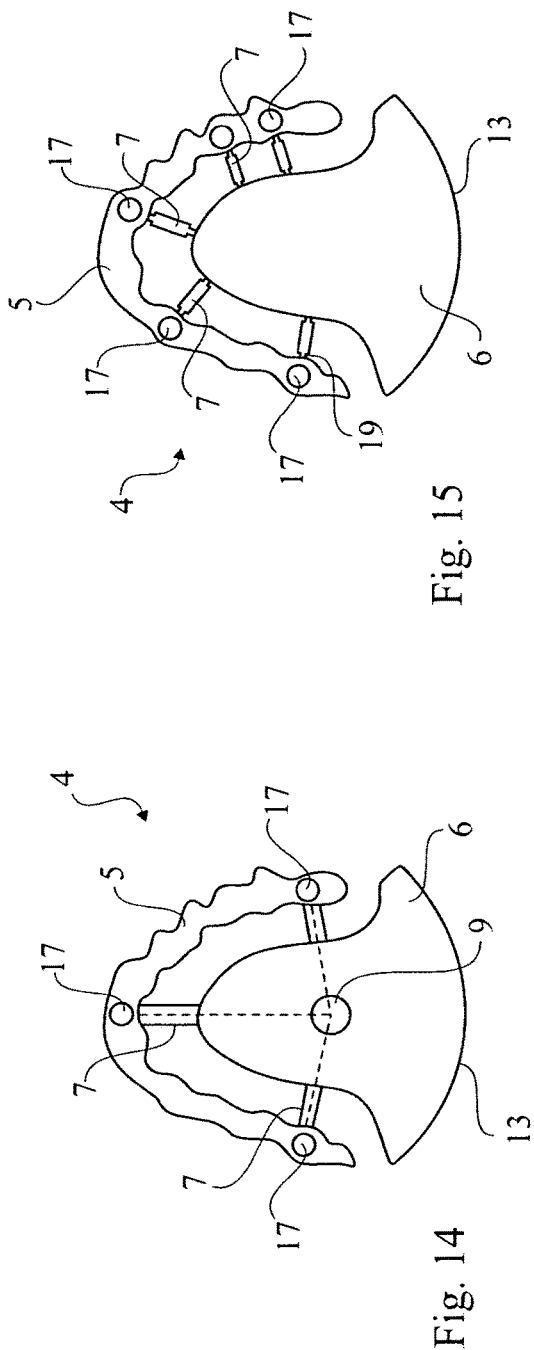

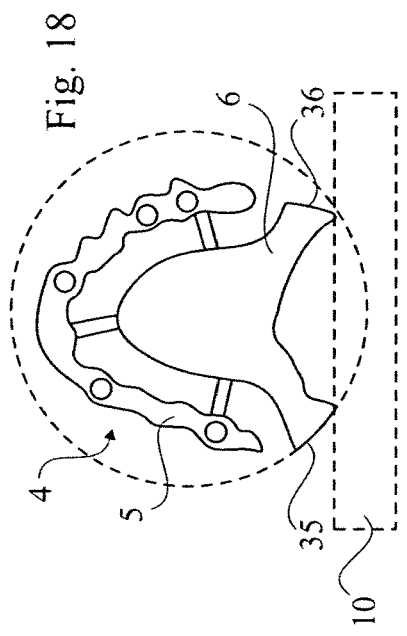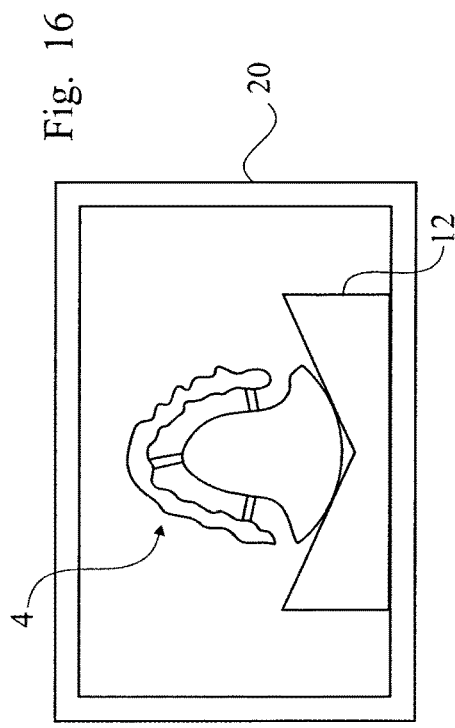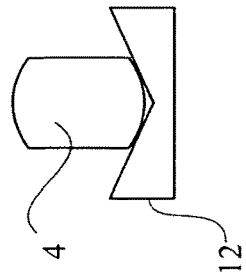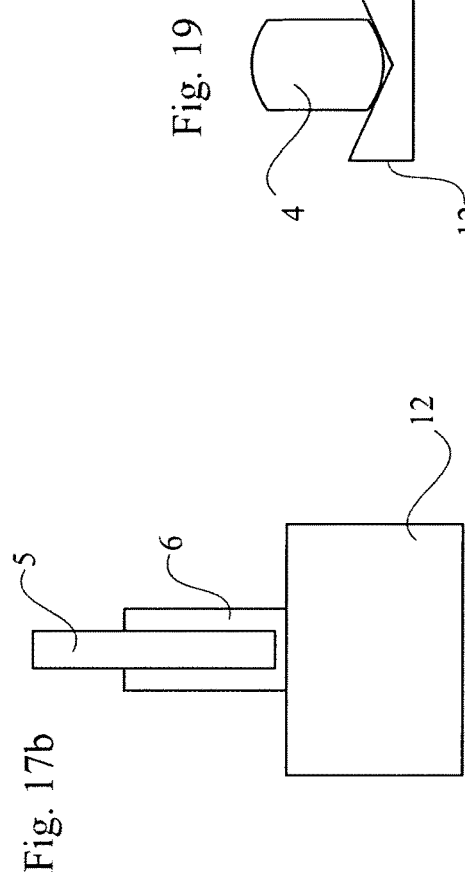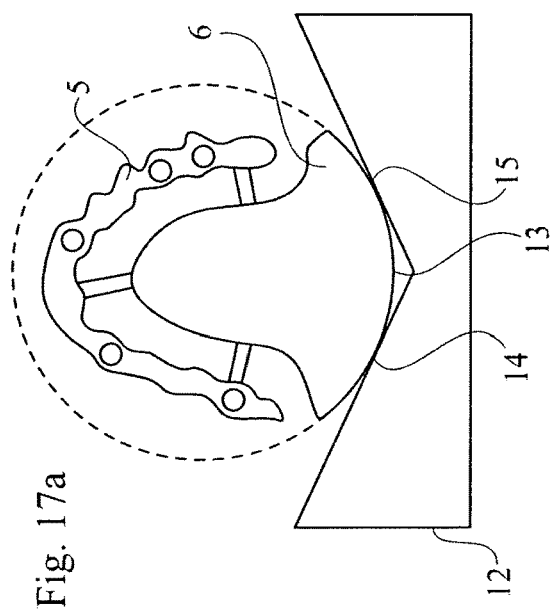

METHOD AND ARRANGEMENT FOR FORMING A DENTAL BRIDGE

CROSS-REFERENCE TO RELATED APPLICATIONS

This application is a national stage application under 35 U.S.C. § 371 of PCT Application No. PCT/EP2008/004245, filed on May 29, 2008, which published in English as WO 2008/148495 A1 on Dec. 11, 2008 and which claims priority benefit of European Patent Application No. 7011196-8, filed on Jun. 7, 2007, the entire contents of which applications and publication are herein incorporated by reference in their entirety.

BACKGROUND

Field of the Invention

The present application relates to a method and an arrangement for manufacturing a dental bridge of the kind used to replace missing teeth in the mouth of a patient. The application also relates to an intermediate product used in the process of manufacturing such a dental bridge.

Description of the Related Art

Dental bridges are used to replace missing teeth on a patient's jaw. Such a bridge may be manufactured in a process that includes sintering of powder into a body that may subsequently be formed in a machining operation that may include, for example, milling, turning, grinding or drilling. An example of such a method is disclosed in WO 2006/025778. In that document, a method for producing a bridge structure from a ceramic blank is disclosed. The document discloses, inter alia, that machining of a bridge structure may be performed on material that is in a pre-sintered state. When a dental bridge structure is manufactured, it is desirable that the bridge structure can be made with a high degree of precision since it is normally made to fit a specific patient. Therefore, it is an object of certain embodiments of the present invention to provide a manufacturing method that is capable of achieving a high precision. It is also an object to provide an arrangement for carrying out such a method. A further object is to provide an intermediate product suitable for making a dental bridge.

SUMMARY

The present application relates to a method of manufacturing a dental bridge. In certain embodiments described herein, the method comprises the step of providing a blank in the form of a pre-sintered product that has been formed in an initial first sintering operation. The pre-sintered product may have been formed in a process where a green body is subjected to an elevated temperature. In the context of this application, a green body in certain embodiments should be understood as a ceramic body that has been formed by pressing ceramic powder to a solid body. Due to the first sintering operation, the pressed green body becomes more solid. After the first sintering operation, the green body has been transformed into a pre-sintered object. However, the pre-sintered object has not yet reached its final density. A machining operation is performed on the blank, normally the pre-sintered object, that transforms it to an intermediate product comprising in certain embodiments, a bridge structure and a support body linked to the bridge structure by one or several retaining sections that extend from the support body to the bridge structure. Such retaining sections may be shaped as spokes. A sintering operation is then performed on the intermediate product. In some embodiments, the retaining section or retaining sections still link(s) the bridge structure to the support body during the second sintering operation, thereby supporting the bridge structure during the second sintering operation. The retaining sections may be removed from the bridge structure after the second sintering operation. Optionally, the method may be performed in such a way that, during the second sintering operation, the intermediate product has been placed such that the retaining sections(s) extend(s) at least partially in a vertical direction.

The method may be performed in such a way that the bridge structure is supported only by the retaining section(s) during the second sintering operation.

In some embodiments, the bridge structure may form an arch while the intermediate product comprises several retaining sections (e.g. spokes) that connect the support body to the bridge structure. At least some of the retaining sections may then extend from the bridge structure towards a common hub in the support body.

Before the first sintering operation, the green body may have been given many different shapes. For example, it may have been shaped as a body having a circular cylindrical cross section.

If the blank from which the intermediate product is made has a circular cylindrical shape, the support body of the intermediate product may optionally retain a part of the circular cylindrical cross section. In this way, the support body can have an exterior surface that forms a circular arc.

During the second sintering operation, the intermediate product may optionally be placed such that it stands upright resting on an edge. It may also be placed such that it rests against a surface that is slanted/inclined relative to the horizontal plane. This can be done in such a way that the entire intermediate product or a major part of it rests against an inclined surface. As an alternative, the support body may rest on a V-block in such a way that the exterior surface of the support body abuts the V-block at two places along the circular arc.

Instead of lying on an inclined surface when it is sintered (e.g., during the second sintering operation), the intermediate product may rest on elements shaped as solids of revolution.

When the intermediate product is sintered (e.g. during the second sintering operation), the intermediate product may be placed, e.g., oriented, such that the retaining sections extend in an essentially vertical direction.

The bridge structure is typically adapted to be supported by such structure as, for example, a dental implant, a preparation or an implant supported abutment when the bridge structure is finally placed in the mouth of a patient. Therefore, the bridge structure may optionally have at least one part shaped to fit a structure such as a dental implant, an implant supported abutment or a dental preparation, e.g., shaped to define an interface for such a structure. When this is the case, the intermediate product may be shaped such that at least one retaining section extends from the support body to the part shaped to define an interface for a structure such as a dental implant, an implant supported abutment or a dental preparation or to an area adjacent the part shaped to define an interface such that the retaining section becomes associated with the part shaped to define an interface. It should be understood that for certain embodiments, the bridge structure may have several parts shaped to define interfaces. In such cases, each part shaped to define an interface may have at least one associated retaining section.

The retaining section(s) or one of the retaining sections (if several are used) may be shaped to have a reduced cross section where it meets at least one of the support body and the bridge structure. For example, one of the retaining sections could have a reduced cross section where it meets the support body or it could have a reduced cross section where it meets the bridge structure. It would also be possible that one or several retaining sections have a reduced cross section at both ends.

The application also relates to an arrangement for manufacturing a dental bridge. In certain embodiments, the arrangement comprises at least one heating furnace in which a ceramic material may be sintered or where a previously formed body may undergo an additional sintering operation. In certain embodiments, the arrangement further comprises a sintering support on which a previously sintered object may rest during the additional sintering operation. The sintering support comprises at least one of a plurality of elements shaped as bodies of revolution or a sintering support which, when placed in the heating furnace, may present at least one surface that is inclined relative to the horizontal plane. The sintering support may be a V-block.

The arrangement for manufacturing a dental bridge may optionally comprise a mold that defines a circular cylindrical shape such that ceramic material may be formed into a circular cylindrical body in the mold.

Certain embodiments of the invention also relate to a sintered product suitable for making a dental bridge. The sintered product has been created by machining a pre-sintered blank to a desired shape and subsequently sintering the machined blank. In certain embodiments, the sintered product has a density in the range of 6.0-6.1 g/cm$^3$. In certain embodiments, the sintered product comprises a bridge structure and a support body linked to the bridge structure by one or several retaining sections that extend from the support body to the bridge structure. The sintered product can be used to make a dental bridge through a procedure that includes removal of the support body and the retaining section(s) from the bridge structure. After removal of the retaining section(s) from the bridge structure, remnants of the retaining section(s) can be eliminated (or reduced) by, for example, grinding.

BRIEF DESCRIPTION OF THE DRAWINGS

FIG. 1 is an example schematic representation of how an object may be subjected to an initial sintering operation in a furnace.

FIG. 2 is an example schematic representation of an arrangement that may be used during pressing of the green body.

FIG. 3 shows a cross section of the arrangement shown in FIG. 2 together with a pressure chamber and a pressure medium in which the arrangement of FIG. 2 may be placed.

FIGS. 6-11 show different embodiments of an intermediate product that has been created by machining an object that is rectangular or formed from a cylinder where parts of the cylinder have been removed.

FIGS. 12-15 show different embodiments of an intermediate product that has been created by machining a circular cylindrical body.

FIG. 16 is an example schematic representation of how an intermediate product that has been machined is placed in a sintering furnace once again for a final sintering operation.

FIGS. 17-24 show different examples of how an intermediate product may be supported on a sintering support during the final sintering operation.

DETAILED DESCRIPTION

With reference to FIG. 1, a method for manufacturing a dental bridge may comprise subjecting an object 3 to a first sintering operation where sintering can be performed in a sintering furnace 20. The first sintering operation can be understood as pre-sintering where the object 3 does not reach its final density. Typically, the density of the object 3 increases only slightly during the first sintering operation and in some cases it may actually be so that density does not at all increase during the first sintering operation. During the first sintering operation, the object that is sintered may be subjected to a temperature of, for example, about 800° C.-1200° C. for a period of 1-2 hours. The object 3 that is sintered is made of a ceramic powder material 2, for example zirconium oxide or aluminum oxide. Before the sintering operation, the powder material 2 may have been compressed in a mold 30 into a solid green body as indicated in FIG. 2. The mold 30 may be, for example, a mold that is shaped to form circular cylindrical objects. Such a mold 30 is shown in perspective in FIG. 2. The powder material may be mixed with a binding agent before it is put inside the mold 30 and compressed.

Figure 4A:
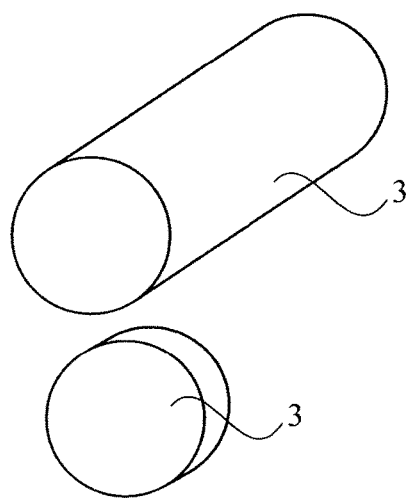
FIG. 4a shows examples of green bodies with a cylindrical cross section.
Figure 4B:
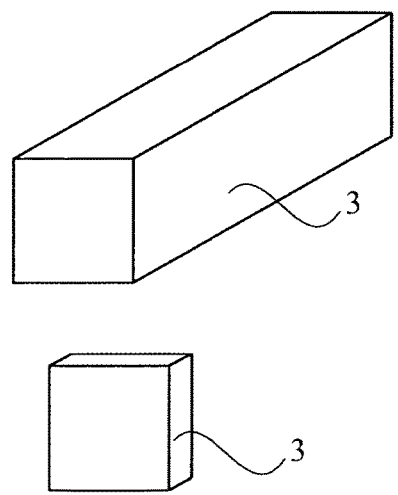
FIG. 4b shows examples of green bodies with a rectangular cross section.

With reference to FIG. 2 and FIG. 3, the mold 30 may be a sleeve made of an elastomer, e.g. rubber. The sleeve may be filled with ceramic powder 2 and placed in a chamber 100 that is filled with a liquid L which can be pressurized. The liquid L is pressurized and the pressure acts from all directions on the sleeve, as indicated by the arrows in FIG. 3, such that the powder is compressed uniformly and pressed into a green body 3 that may subsequently be sintered. It should be understood that mold 30 may have many other shapes and that the arrangement shown in FIG. 2 and FIG. 3 is only an example of a possible arrangement for pressing green bodies. With other arrangements, ceramic powder may be formed into, for example, objects 3 having a rectangular cross section as indicated in FIG. 4b. Of course, may other shapes would be possible. For example, objects 3 with an elliptical cross section are also possible.

Figure 5:
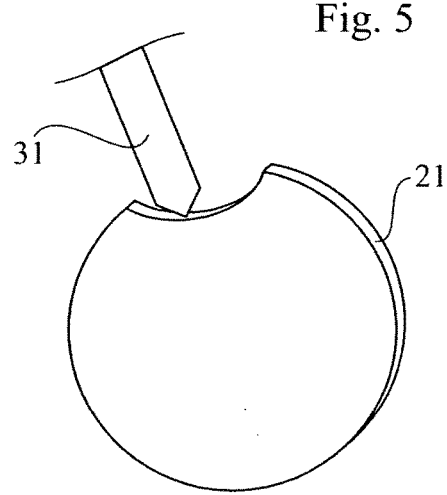
FIG. 5 is an example schematic representation of how an object that has been subjected to an initial sintering operation is subjected to a machining operation.

During the first sintering operation, or initial sintering operation, the green body 3 is placed in the furnace 20 in certain embodiments and subjected to an elevated temperature such that the green body 3 thereby becomes more solid, e.g., it becomes a pre-sintered blank. In the following, the reference numeral 21 will be used for the pre-sintered blank while the reference numeral 3 is used for the green body that has not yet been sintered. In certain embodiments, it shall be understood that the first sintering operation transforms the green body 3 into the blank 21. The blank 21 in certain embodiments will have substantially the same shape as the green body from which it has been created. After sintering, it will be possible to subject the blank 21 to a machining operation as symbolically indicated in FIG. 5. The density for a zirconium oxide blank that has been pre-sintered may typically be about 3.0-3.3 g/cm$^3$. In FIG. 5, a machine tool is indicated by the reference numeral 31. In practice, the machining operation may be, for example, milling, turning, grinding or drilling. The tool 31 in FIG. 5 may thus be seen as a symbolic representation of, for example, a milling tool. The first sintering operation is performed in such a way that the object 3 does not reach its final density but the resulting blank 21 is still soft enough to be easily machined. The machining operation transforms the blank 21 into an intermediate product 4. Some examples of such an intermediate product are shown schematically in FIGS. 6-11. In the embodiments shown in FIGS. 6-11, the intermediate product 4 may have been formed from a blank 21 that has a rectangular cross section. As an alternative, FIGS. 6-11 could be understood as representing objects formed from an originally circular cylindrical blank where parts of the blank have been cut away to give the blank two opposing flat surfaces. With reference to FIG. 6, the intermediate product 4 comprises a bridge structure 5 that will eventually become a dental bridge 1 that can be placed in the mouth of a patient. In certain embodiments, the intermediate product 4 also comprises a support body 6 linked to the bridge structure 5 by one or several retaining sections 7 that extend from the support body 6 to the bridge structure 5. The retaining sections 7 may be shaped as spokes or rods.

Figure 8C:
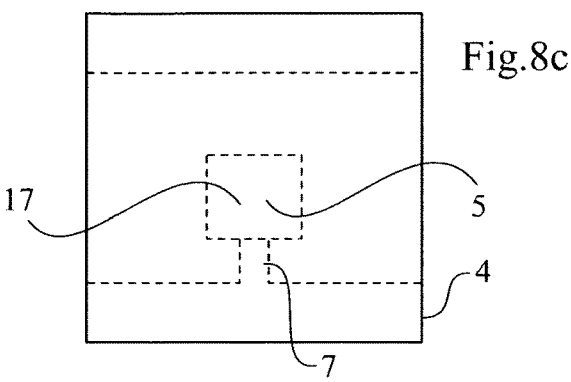

In the embodiment of FIG. 7, the retaining sections 7 are also shown as spokes but they are oriented in a somewhat different way compared to the orientation in FIG. 6. The embodiment of FIG. 8a is, in principle, identical to the one shown in FIG. 6 but, during the second (e.g., the final) sintering, the intermediate product 4 is turned upside down compared to the position of FIG. 6. The embodiment of FIG. 9 differs from that of FIG. 7 in that some of the retaining sections 7 are pointing in a partially upward direction in FIG. 9. In for example FIG. 6 and FIG. 8a, the intermediate product is presented in a front view. With reference to FIG. 8b and FIG. 8c, the three-dimensional shape of the intermediate product will be more easily understood. With reference to FIG. 8c, it can be seen that the intermediate product 4 can be formed in such a way that the bridge structure 5 can be completely contained within the outer contours of the support body 6. In this way, the intermediate product 4 can be placed on a planar supporting surface without risk that the bridge structure contacts the supporting surface which could lead to unwanted frictional forces. With the intermediate product 4 placed upright and standing on its lower edge 40, the bridge structure 5 can be supported by the retaining sections 7 that extend in a substantially vertical direction. This reduces deformation due to the force of gravity when the second sintering operation is performed.

Figure 10:
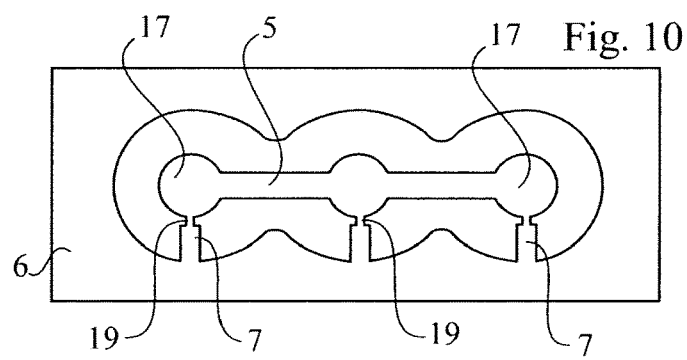
Figure 11:
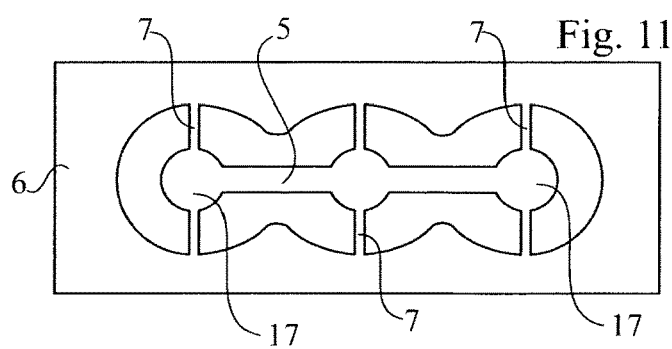

In the embodiment of FIG. 10, the retaining sections 7 are shaped as spokes that have a part 19 at the end near the bridge structure 5. The part 19 has a reduced cross section compared to the rest of the retaining section 7. In the embodiment of FIG. 11, more than one retaining section 7 connects the support body to a specific part 17 of the bridge structure 5.

In the embodiments shown in FIGS. 6-11, the bridge structure 5 is shown as a substantially straight bridge structure. Such a bridge structure 5 may be suitable where only a few teeth are to be replaced in a patient's mouth. However, some patients may need a longer dental bridge. In FIGS. 12-15, embodiments are shown where the bridge structure 5 forms an arch that may cover an essential part of a patient's upper or lower jaw. The embodiments shown in FIGS. 12-15 may suitably be formed from a pre-sintered object (blank) having a cylindrical cross section but could also be formed from pre-sintered objects (blanks) with a different shape.

Figure 9:
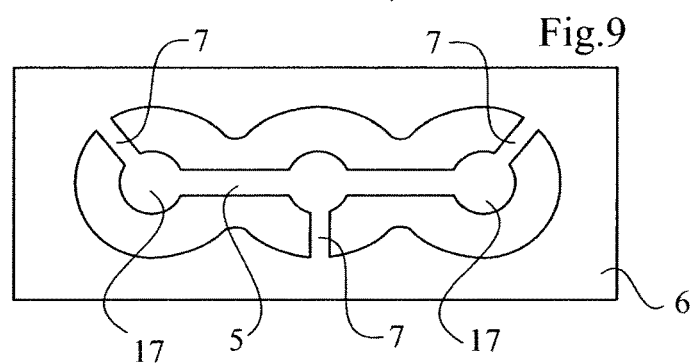

When the intermediate product 4 has been formed, it can be placed in a sintering furnace 20 and sintered again. The sintering furnace may be the same sintering furnace 20 used for the first sintering operation but it could also be a separate sintering furnace. The second sintering operation may be performed at a temperature in the range of 1200° C. to 1650° C. For example, the second sintering operation may be performed at a temperature of 1500° C. during 2 hours. For the second sintering operation in certain embodiments, the intermediate product 4 is placed in a position where the retaining sections 7 (for example spokes 7) extend at least partially in a vertical direction. This can be done by placing the intermediate product 4 standing up on one of its edges. With reference to FIG. 8a and FIG. 8b, the intermediate product 4 is shown standing up such that the bridge structure 5 is resting on the retaining sections 7 (e.g. spokes). The retaining sections 7 are standing upright and extend in a vertical direction. They will thus carry the bridge structure 5. In certain embodiments, while the intermediate product is placed in that position (e.g., standing), the second sintering operation is performed. The second sintering operation is a final sintering operation in certain embodiments during which the bridge structure 5 will become more solid and hard enough to be placed in the mouth of a patient, e.g., it will reach its final density. The final density may typically be about 6.0-6.1 g/cm$^3$ for objects based on zirconium oxide. During the second sintering operation, the ceramic material will be subjected to the force of gravity which may cause deformation of the bridge structure 5. Since the bridge structure 5 is resting directly on the retaining sections 7 in certain embodiments, the force of gravity will be carried by the retaining sections 7 as a pressure stress and the deformation of the structure will be smaller than if the intermediate product had been lying down in such a way that the retaining sections had been exposed to a bending stress. In certain embodiments, the pre-sintered material in the retaining sections 7 (and the bridge structure 5) can resist pressure stress quite well but is more sensitive to bending stress. The same is true also for the embodiment of FIG. 7, even though some of the retaining sections 7 are shown as being inclined relative to the vertical direction. In FIG. 6, the intermediate product has been placed in such a way that the bridge structure 5 is hanging in the retaining sections 7 (that may be shaped as spokes) while FIG. 9 shows an embodiment where a middle part of a bridge structure 5 is resting on a retaining section 7 and two end parts are shown as suspended in inclined retaining sections 7. The retaining section(s) 7 will thus be in place during the second sintering operation. In certain embodiments, the retaining section or retaining sections 7 will then support the bridge structure 5 and counteract deformation of the bridge structure 5 during the second sintering operation.

After the second sintering operation, the retaining section(s) 7 is/are removed from the bridge structure 5 in certain embodiments. This can be done more easily if the retaining section(s) is/are somewhat weaker near the bridge structure 5, e.g., at an end of the retaining sections 7 that is adjacent the bridge structure 5. In FIG. 10, it is shown how retaining sections 7 may have a part 19 that is less thick, e.g., has a smaller cross section. This will not only make it easier to break the retaining sections, it also makes it easier to remove remnants 50 of the retaining sections 7 when the bridge structure has been separated from the support body 6. Remnants 50 of the retaining sections may be removed by, for example, grinding.

Certain embodiments of the invention will now be further explained with reference to FIGS. 12-15. In FIGS. 12-15, the bridge structure 5 forms an arch that is intended to cover a larger part of a patient's mouth and could possibly be used in cases where all or substantially all the teeth in a patient's upper or lower jaw must be replaced by a bridge. As seen in the figures, the bridge structure forms an arch 8 and the intermediate product 4 comprises several retaining sections 7 that connect the support body 6 to the bridge structure 5. The embodiments shown in FIGS. 12-15 may be formed from a body 3 that has a circular cylindrical cross section as indicated in FIG. 4a. Such a shape may have a more uniform density and thus more uniform properties of strength compared to a body having for example a rectangular cross section. The reason is that, when the body is originally formed in a mold 30, the pressure can be more uniformly distributed in the mold if the mold defines a circular cylindrical cavity.

With reference to FIG. 13 and FIG. 14, some of the retaining sections 7 are shaped as spokes that extend from the bridge structure 5 towards a common hub 9 in the support body 6. The common hub 9 can be understood as an imaginary point in the support body 9. In certain embodiments, this design leads to a more even distribution of forces and will contribute to keeping the shape of the structure such that the force of gravity will cause less deformation during sintering.

It is not only the force of gravity that may cause deformation during the second sintering operation. Deformation may also be caused by frictional forces. This is, of course, true both for the embodiments shown in FIGS. 6-11 and the embodiments of FIGS. 12-15. In certain embodiments, when the intermediate product 4 is sintered, it will shrink to some degree and all contact with other objects (such as a support) may cause frictional forces. If the bridge structure 5 should rest directly on a support during the second sintering operation (e.g., a support separate from the support body 6 or the retaining section(s) 7), forces due to friction between the bridge structure 5 and the support could cause deformation of the bridge structure. To prevent this from happening, the intermediate product 4 may be placed such that the bridge structure 5 is supported only by the retaining section(s) 7 during the second sintering operation. If the bridge structure 5 is supported only by the retaining section(s) 7, frictional forces acting directly on the bridge structure may be avoided.

However, deformation may be further reduced if also frictional forces acting on the support body 6 can also be reduced during the second sintering operation. Some different ways of reducing frictional forces during the second sintering operation shall now be explained in the following.

In the embodiments of FIGS. 12 and 14-15, the support body 6 of the intermediate product 4 retains a part of the circular cylindrical cross section such that the support body 6 has an exterior surface 13 that forms a circular arc. During the second sintering operation, the support body 6 may be placed such that it is resting on a V-block 12 as indicated in FIGS. 16 and 17a. In certain embodiments, the exterior surface 13 of the support body 6 will then abut the V-block 12 at two places 14, 15 along the circular arc. These two places are seen as points in FIG. 17 but it should be understood that for certain embodiments, the contact points 14, 15 will be lines of contact between an inclined surface 11 of the V-block 12 and the exterior surface 13 of the support body 6. Since there is physical contact only at the two points (or lines of contact) 14, 15 and since the V-block 12 offers an inclined contact surface 11, the contact between the intermediate product 4 and the V-block 12 is reduced and the effect of friction will thus be relatively low. In FIG. 17b, a side view is presented of the V-block and the intermediate product of FIG. 17a. It can thus be understood from FIGS. 17a and 17b that the retaining sections 7 (e.g. spokes 7) extend at least partially in a vertical direction and are thus able to support the bridge structure 5 effectively such that the force of gravity will not cause so much deformation during the second sintering operation.

It should be understood that a V-block 12 may also be used for the kind of intermediate product 4 shown in FIGS. 6-11. Such a possibility is indicated in FIG. 19. As indicated in FIG. 19, the intermediate product may still have arch-shaped sides although it is substantially rectangular. Such a shape may be the result of a manufacturing process where a body with a circular cylindrical cross section has been machined such that it obtains mutually opposing flat surfaces.

Figure 20:
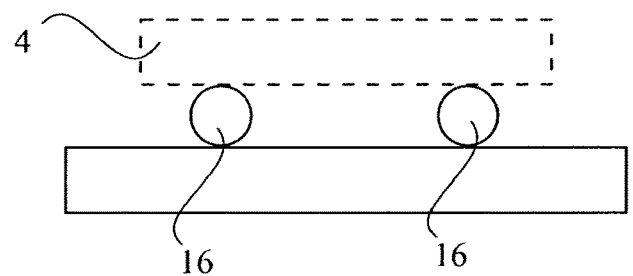
Figure 21:
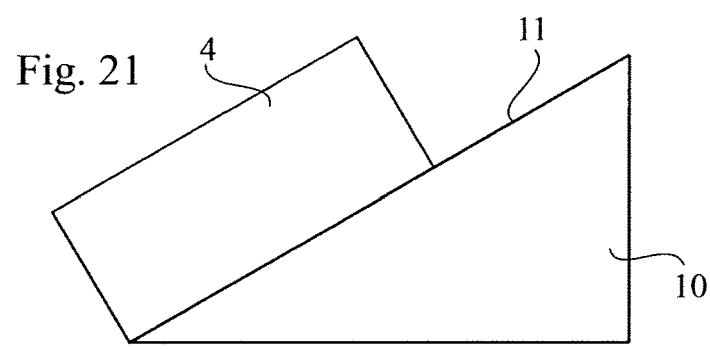
Figure 22:
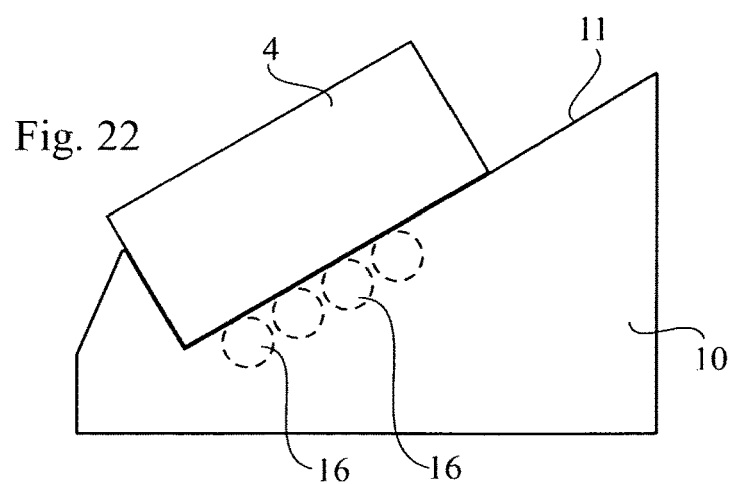
Figure 24:
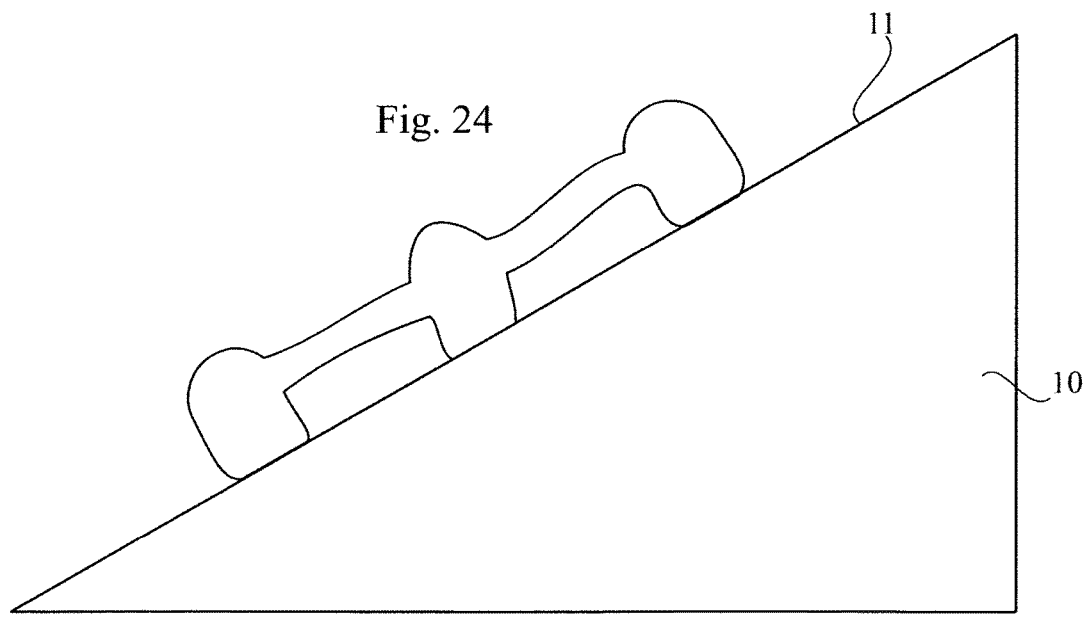

The use of a support with an inclined surface 11 can also be achieved by other means than a V-block 12. In FIGS. 21 and 22, examples are shown of sintering supports 10 that may present a support surface 11 that is slanted or inclined relative to the horizontal plane when the sintering support 10 is used during the sintering operation, e.g. when the sintering support 10 is placed in a sintering furnace 20. In FIG. 21 and FIG. 22, an intermediate product 4 is indicated which is placed on an inclined surface 11 of a sintering support 10. This reduces the effect of friction. The object placed on an inclined surface may be, for example, an intermediate product 4 such as shown in FIGS. 6-11 but there are also other possibilities. For example, it would in principle be possible to make a bridge structure 5 without any special support body 6 and retaining sections 7. Such a bridge structure 5 could then be placed directly on a sintering support 10 with an inclined surface as schematically indicated in FIG. 24. In such a procedure, the force of gravity may cause more deformation but the impact of frictional forces is reduced since the bridge structure rests on an inclined surface. It should thus be understood that the principle of reducing friction may be used independently of whether anything is done to counteract the effects of the force of gravity or not. Instead of using an inclined plane, the sintering support 10 could comprise elements 16 shaped as solids of revolution on which the intermediate product 4 could rest in order to reduce friction. Such a solution is schematically indicated in FIG. 20. The elements 16 that are shaped as solids of revolution may be, for example, rolls or spheres but other shapes may also be possible. Such elements could also be used in combination with an inclined surface as indicated in FIG. 22. With reference to FIG. 20, it should be noted that embodiments are possible where the retaining sections will actually extend entirely in a horizontal plane. In FIG. 20, the intermediate product 4 is actually lying flat on the sintering support. Although the retaining elements as such are not visible in FIG. 20, it will be understood that in certain embodiments they are not extending in a vertical direction when the intermediate product is in this position. When the retaining sections do not at all extend in a vertical direction but lie in a horizontal plane, they can still have some capacity to counteract the force of gravity since they may still give a degree of support for the bridge structure during the second sintering operation.

In order to reduce deformation during the second sintering operation as much as possible, the intermediate product 4 may be placed such that the bridge structure 5 is supported by the retaining sections 7 that extend in an essentially vertical direction or that at least one retaining section 7 extends in an essentially vertical direction.

With reference to FIG. 13 and FIG. 14, one retaining section 7 (or several retaining sections 7) may be placed such that they are oriented in a vertical plane when the intermediate product 4 is standing on its support body 6 and such that they extend in an at least partially vertical direction. One or several such retaining sections may even be oriented in a completely or almost completely vertical direction. If such a vertical or essentially vertical retaining section 7 is placed at the center of the arched bridge structure 5 as indicated in FIGS. 13 and 14, the ability of the structure to withstand gravitational force with a minimum of deformation will be even greater.

In FIG. 18, an example solution is showed where the sintering support 10 is shaped to present a planar support surface for the intermediate product 4. However, the support body 6 of the intermediate product 4 does not have the arched surface 13 shown in for example FIG. 12. Instead, it has two separate legs 35, 36 such that in certain embodiments, there will only be two contact points (or lines of contact) between the sintering support 10 and the intermediate product 4. Hence, forces due to friction will not have such a great influence on the intermediate product during the second sintering operation. As a consequence, deformation due to frictional forces is reduced and the final products can thus be manufactured with a higher precision. With the shape shown in FIG. 18, no separate sintering support 10 is needed and the intermediate product 4 can be placed directly in a heating furnace (sintering furnace). In order to minimize friction, the planar support surface may have been treated by, for example, grinding in order to reduce surface roughness and thereby friction.

Figure 23A:
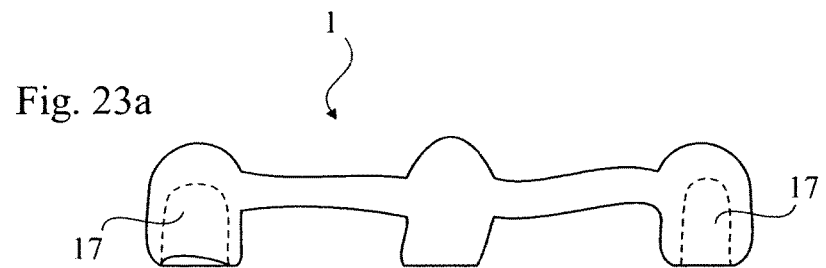
Figure 23B:
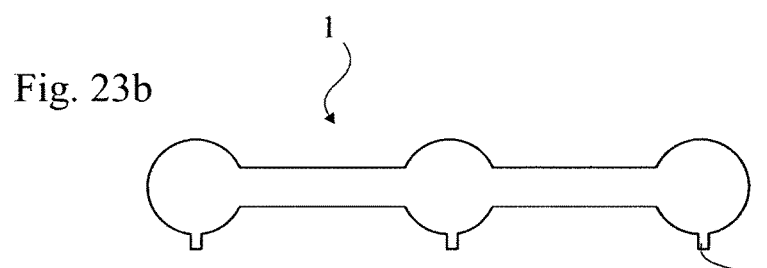
Figure 23C:
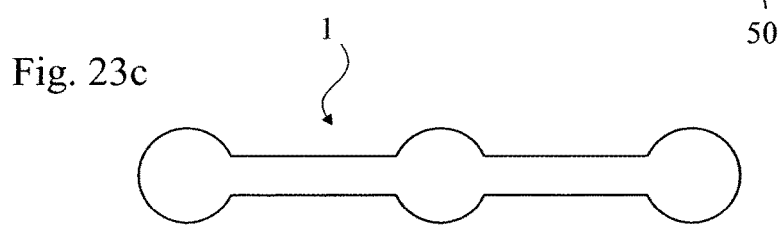

With reference to FIG. 23a, the final product in the form of a dental bridge 1 will typically have one or several parts 17 where the part 17 (or each part 17) is shaped to define an interface for a dental implant, an implant supported abutment or a dental preparation, e.g., to fit such a structure. For example, the dental bridge shown in FIG. 23a may be a bridge having parts 17 that are shaped to be placed over a dental preparation or an implant supported abutment. Parts 17 of the bridge structure 5 that presents such interfaces are made to fit the geometry of a specific patient. Therefore, it is especially desirable that the second sintering operation does not cause such deformation that alters the position of the parts 17 that define such interfaces (e.g. interfaces for dental implants or dental preparations), e.g., the position of these parts relative to each other. It is regarded as desirable that the location of each interface part 17 in certain embodiments does not deviate more than 50 μm from the previously calculated position that fits the patient's oral structure. Consequently, in certain embodiments, it may be more important to ensure that the interface parts 17 stay in place than the rest of the bridge structure 5. For this reason, the retaining sections 7 may optionally be placed such that at least some of the bridge parts 17 that define interfaces are directly connected to and supported by a retaining section 7. In practice, this means that the retaining section 7 extends from the support body 6 to a part 17 of the bridge structure 5 that is shaped to define an interface for a dental implant, an implant supported abutment or a dental preparation.

In some embodiments, the bridge structure 5 comprises several parts 17 shaped to define interfaces and each part 17 shaped to define an interface has at least one associated retaining section 7. Such an embodiment can be seen in, for example, FIG. 14. With reference to FIG. 11, it should also be understood that more than one retaining section 7 may be associated with a part 17 that defines an interface.

With reference to FIG. 15, it can be seen that, also in embodiments with an arch-shaped bridge structure, one or several retaining sections 7 may have a part 19 with a reduced cross section where the retaining section 7 meets at least one of the support body 6 and the bridge structure 5. With the exception of the part 19 with reduced cross section, the retaining sections may have a cross sectional area of, for example, 0.5 mm$^2$-20 mm$^2$ (depending on the specific requirements of each particular case). In for example FIG. 10 and FIG. 15, the part 19 that has a reduced cross section is indicated schematically as a sudden reduction or weakening of the retaining section(s). However, it should be understood that there are also other possibilities and one other possibility is shown in FIG. 13 where the retaining sections are shaped as spokes that gradually become thinner towards the bridge structure 5.

With reference to FIG. 16, it should be understood that the present application may also relate to an arrangement for manufacturing a dental bridge 1. In certain embodiments, the arrangement comprises at least one heating furnace 20 in which a ceramic material may be formed into a solid blank 21 having a predetermined shape or where a previously sintered object may undergo an additional sintering operation. The arrangement may further comprise a sintering support 10 on which a previously formed intermediate product may rest during the additional sintering operation. The sintering support in certain embodiments comprises at least one of a plurality of elements 16 shaped as bodies of revolution or a sintering support 10 which, when placed in the heating furnace, may present at least one surface 11 that is inclined relative to the horizontal plane as has been explained previously. The sintering support 10 may take the shape of a V-block 12.

The arrangement may also comprise a mold, for example a mold that defines a circular cylindrical shape such that ceramic material may be formed into a circular cylindrical green body 3 in the mold 30.

When friction is reduced, deformation due to frictional forces will also be reduced and the precision in the final product becomes higher.

It should be understood that, as the method is performed in practice, the forming of the green body and the first sintering operation may be performed by a manufacturer of blanks that are later delivered to a manufacturer of dental bridges. The actual manufacturing of the dental bridge can then be described in terms of first providing a pre-sintered blank made from a green body of ceramic material, performing a machining operation on the pre-sintered blank such that the pre-sintered blank is transformed into an intermediate product comprising a bridge structure and a support body linked to the bridge structure by one or several retaining sections that extend from the support body to the bridge structure and subsequently performing a sintering operation on the intermediate product while the retaining section(s) still link the support body to the bridge structure.

In the examples shown, the retaining sections have been shown as spokes or rods. However, it should be understood that the retaining sections may have many different shapes as long as they are able to support the bridge during the second sintering operation. In principle, it could even be so that there is only one retaining section in the form of a thin sheet that extends between the bridge structure and the support.

By having one or several retaining sections during the second sintering operation, it is possible to give support to the bridge structure during the second sintering operation. This may counteract deformation due to friction and/or the force of gravity. As a result, precision in manufacturing can be higher.

It should also be understood that the use of various means for reducing or elimination friction during the second sintering operation may be used independently of whether retaining sections are used or not. Embodiments are thus conceivable where such retaining sections are not at all used.

It should be understood that different solutions disclosed in this application may well be combined with each other.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A method of manufacturing a dental bridge, the method comprising: providing a pre-sintered blank of ceramic material, wherein the pre-sintered blank was treated with a uniform pressing process on a powder material mixed with a binding agent; performing a machining operation on the blank that transforms the blank into an intermediate product comprising a bridge structure and a support body linked to the bridge structure by a plurality of retaining sections that extends from the support body to the bridge structure; and performing a sintering operation on the intermediate product while the plurality of retaining sections still links the support body to the bridge structure, wherein the bridge structure forms an arch and the plurality of retaining sections is shaped as spokes that extend from the bridge structure towards a common hub in the support body, wherein a portion of the support body where the retaining sections extend from the common hub has an exterior surface that forms a curved shape, wherein one or more retaining sections of the plurality of retaining sections comprise a first part and a second part, the second part disposed between the first part and the bridge structure, wherein the one or more retaining sections have a cross section that reduces from the first part to the second part in a step like manner, and wherein during the sintering operation performed on the intermediate product, the intermediate product is standing on the support body and is provided with at least one retaining section of the plurality of retaining sections extending at least partially in a vertical direction.

2. A method according to claim 1, in which the at least one retaining section is removed from the bridge structure after the sintering operation.

3. A method according to claim 1, in which the bridge structure is supported only by the at least one retaining section during the sintering operation.

4. A method according to claim 1, in which a part of the support body of the intermediate product has an exterior surface that forms a circular arc.

5. A method according to claim 4, in which, during the sintering operation, the support body is resting on a V-block in such a way that an exterior surface of the support body abuts the V-block at two places along the circular arc.

6. A method according to claim 1, in which, during the sintering operation, the intermediate product is resting against a surface that is slanted relative to the horizontal plane.

7. A method according to claim 1, in which, during the sintering operation, the intermediate product is resting on elements shaped as solids of revolution.

8. A method according to claim 1, in which the method includes machining the blank to such a shape that, in the intermediate product, the bridge structure will have at least one part shaped to define a dental interface.

9. A method according to claim 8, in which the at least one retaining section extends from the support body to the bridge structure such that the at least one retaining section is associated with the at least one part that is shaped to define a dental interface.

10. A method according to claim 8, in which the bridge structure comprises a plurality of parts shaped to define dental interfaces and each part shaped to define a dental interface has at least one associated retaining section.

11. A method according to claim 8, in which the dental interface is for a dental implant, an implant supported abutment, or a dental preparation.

12. A method according to claim 1, in which the one or more retaining section has a reduced cross section where it meets at least one of the support body and the bridge structure.

13. A method according to claim 1, in which the blank comprises Zirconia.

14. A method according to claim 1, in which the blank comprises Aluminium Oxide.

15. A method according to claim 1, wherein the pre-sintered blank has a density in a range of 3 to 3.3 $g/cm^3$, and wherein the sintered product has a density in a range of 6 to 6.1 $g/cm^3$.

* * * * *